United States Patent [19]
Murayama et al.

[11] Patent Number: 5,891,192
[45] Date of Patent: Apr. 6, 1999

[54] ION-IMPLANTED PROTEIN-COATED INTRALUMENAL IMPLANTS

[75] Inventors: Yuichi Murayama; Fernando Vinuela, both of Pacific Palisades, Calif.; Yoshiaki Suzuki; Masaya Iwaki, both of Wako, Japan

[73] Assignee: The Regents of the University of California, Oakland, Calif.

[21] Appl. No.: 861,994

[22] Filed: May 22, 1997

[51] Int. Cl.⁶ ........................................ A61F 2/06
[52] U.S. Cl. ................................................ 623/1
[58] Field of Search .............. 623/1, 2, 11, 12, 623/66; 428/410; 427/2

[56] References Cited

U.S. PATENT DOCUMENTS 5,152,783 10/1992 Suzuki et al. .
5,308,704  5/1994 Suzuki et al. .
5,690,670 11/1997 Davidson ...................... 623/1

OTHER PUBLICATIONS

Ahuja et al., "Platinum coil coatings to increase thrombogenicity: A preliminary study in rabbits" *AJNR* (Jul./Aug. 1993) 14:794–798.

Dawson et al., "Treatment of experimental aneurysms using collagen–coated microcoils" *J. Neurosurgery* (1995) 36(1):133–139.

Iwaki, M., "Formation of metal surface layers with high performance by ion implantation" *Nucl. Inst. Meth. Phys. Res. B37/38* (1989) Elsevier Science Publishers, Amsterdam, pp. 661–666.

Murayama et al., "New surface modification of electrically detachable oil (GDC) by ion implantation into proteins" *Kobunshi Gakkai Yokoshu (Polymer Preprints, Japan)* (1996) 45(3):310. English translation enclosed.

Suzuki et al., "Cell adhesion control by ion implantation into extra–cellular matrix" *Nucl. Instr. and Meth. in Phys. Res. B* (1994) 91:588–592.

Suzuki et al., "Ion implantation into collagen for the subsrate of small diameter artificial grafts" *Kobunshi Gakkai Yokoshu (Polymer Preprints, Japan)* (1996) 45(3):310. English translation enclosed.

*Primary Examiner*—David J. Isabella
*Attorney, Agent, or Firm*—Morrison & Foerster, LLP

[57] ABSTRACT

Ion-implanted protein-coated occlusion coils are described which have essentially the same dimensions as untreated coils and exhibit altered surface properties, e.g., thrombogenicity, endothelial cellular migration and adhesion, relative to untreated coils thus making them particularly useful in treating wide-necked brain aneurysms.

20 Claims, No Drawings

ION-IMPLANTED PROTEIN-COATED INTRALUMENAL IMPLANTS

TECHNICAL FIELD

This invention is in the general field of surgical and endovascular interventional instruments and relates specifically to intralumenal implants such as occlusion coils and stents.

BACKGROUND ART

Occlusion coils are used to occlude a site within a body lumen, such as a blood vessel or Fallopian tube, within the human body. The coil(s) is typically placed at the desired site within the lumen by means of a microcatheter. The coils are normally made of a radio opaque, biocompatible metal such as platinum, gold, or tungsten. In treating brain aneurysms it is common to place a plurality, typically 4 to 12, of coils within the aneurysm. The coils occlude the aneurysm by posing a physical barrier to blood flow and promoting thrombus formation. Ultimately, through healing of the aneurysm sac and re-endothelialization at the neck of the aneurysm a permanent cure of this condition is achieved.

Stents are members, typically tubular shaped, that are placed within body lumens, such as blood vessels, to expand the lumen, provide structural support to the tissue defining the lumen or otherwise repair a segment of the vessel defined by the lumen. Stents may also be placed within vessels by means of microcatheters.

Synthetic polymer or protein coatings have been applied to occlusion coils to enhance their thrombogenicity and wounds healing properties. Ahuja A. A., et al., AJNR Am J. Neuroradiol 14:794–798 (1993) and Dawson, R. C. et al., J. Neurosurgery 36:133 (1995). However, as indicated above, endovascular occlusion techniques generally use small diameter microcatheters to deliver these coils to the occlusion site. Simple polymeric coatings, therefore, result in the problem of increasing the diameter of the coils, which, in turn, may cause them to stick within the microcatheter lumen as they are being delivered. Also, once delivered the coating is subjected to fluid flow within the vessel. If the coating is not solidly fixed to the coil surface it may be dislodged and thus become a potential source of distal thromboemboli.

Ion implantation is a process by which ions are accelerated to a target at energies high enough to bury them below the target's surface. Ion implantation has been applied to the surface of a silicone polymers to alter the thrombogenic properties of the polymer. U.S. Pat. No. 5,152,783. It has also been applied to the surface of polymers such as polystyrene, polyurethane, and extracellular matrix proteins to alter the cellular adhesion properties of the polymer surface. U.S. Pat. No. 5,308,704 and Suzuki, Y. et al., Nucl. Instr. Meth. B. 91:588–592 (1994).

DISCLOSURE OF THE INVENTION

In the present invention a combination of protein coating and ion implantation is used to alter the surface properties of intralumenal implants without substantially increasing their dimensions or changing their physical properties. The improved ability of these novel ion-implanted, protein-coated implants to control thrombosis or effect re-endothelialization and healing make them especially useful in treating wide-necked (neck size greater than or equal to 4 mm) or giant aneurysms in the vasculature of the brain for which uncoated coils have generally proven unsatisfactory.

Accordingly, one aspect of the invention is an intralumenal implant comprising an implant body of a biocompatible material and an ion-implanted protein coating on the body.

Another aspect of the invention is a method for making an ion-implanted protein-coated intralumenal implant comprising:

a) providing an implant body of a biocompatible material;

b) coating the body with a protein to form a protein-coated body; and c) subjecting the protein-coated body to ion implantation.

Yet another aspect of the invention is a method for occluding a site within a mammalian body lumen comprising placing one or more ion-implanted, protein-coated occlusion coils of a biocompatible material at said site.

MODES FOR CARRYING OUT THE INVENTION

All patents, patent applications and other publications cited hereafter are incorporated herein in their entireties.

The implants of the invention may be placed within body lumens, e.g., blood vessels, Fallopian tubes, etc., of any mammalian species, including humans.

Any of the occlusion coils or stents known in the art may be subjected to coating and ion implantation according to the invention. Examples of such coils, without limitation, are those described in U.S. Pat. Nos. 4,994,069; 5,122,136; 5,599,326; 5,582,619; 5,624,461; 5,549,624; and 5,304,194 and European Patent Application/European Patent Application Publications Nos. 0739605 (EPA No. 963029657); 0734697 (EPA No. 963022173); 0765636 (EPA No. 963071584); 0739608 (EPA No. 963029699); 0747014 (EPA No. 963040134); 0747012 (EPA No. 963042189); 0752236 (EPA No. 963049630); PCT/US 93/00882 (EP Pub. No. 07438860); and PCT/US93/09914.

While the implant bodies (e.g. coils and stents) that are coated and ion-implanted according to the invention will normally be made of biocompatible metals such as platinum, gold, tungsten, titanium, tantalum, and the like or alloys of such metals, the bodies may also be made of bioabsorbable or nonbioabsorbable polymers or copolymers. Examples of bioabsorbable polymers that have been used to make intralumenal implants are polyglycolic acid, polyglycolic/poly-L-lactic acid copolymers, polyortheosters, polycaprolactive, polyhydroxybutyrate/hydroxyvalerate copolymers, poly-L-lactide, polydioxanone, polycarbonates, "pseudo" polyamino acids (amino acid polymers in which peptide bonds have been replaced with other linkage groups) and polyanhydrides. Examples of nonbioabsorbable polymers that have been used to make intralumenal implant bodies are polyethylene terephthalate, polyurethane urea, and silicone polymers. Other bioabsorbable and nonbioabsorbable polymers that may be used to make intralumenal implants are described in U.S. Pat. No. 5,527,337; EPA Pub. No. 0604022A1, PCT Pub. No. WO 93/15787; "Biodegradable Stents", Zidar, J. P. et al., Textbook of International Cardiology, 2nd Edition, W. B. Saunders Company (1994) pp. 787–802; "Current Status of Biodegradable Stents", Tanguay, J. F. et al., Cardiology Clinics, Vol. 12, No. 4, W. B. Saunders Company (1994) pp. 699–713; Langer, R., Annals of Biomedical Engineering (1995) 23:101–111; and Pulapura, S. et al., J. Biomater. Appl. (1992) 6(3):216–250.

Preferred proteins for use in the invention are the naturally occurring mammalian cell adhesion proteins. Such proteins contain one or more bonding sites (e.g., the RGD peptide sequence) that is recognized by receptors on various cell types such as platelets, fibroblasts, and endothelial cells. A mixture of such proteins may be used if desired. Examples of cell adhesion proteins are, without limitation, collagen, fibronectin, vitronectin, laminin and fibrinogen. Usually the protein is applied in solution to the implant body by dipping, spraying or other conventional coating techniques. The thickness of the protein coating (after drying) will usually be in the range of 1 to 10 μm.

Any ion may be used that does not have an adverse effect on endothelialization and healing. Examples of ion species that may be used in the invention are $He^+$, $C^+$, $N^+$, $Ne^+$, $Na^+$, $K^+$, $N_2^+$, $O_2^+$, $Kr^+$, $H^+$, and $Ar^+$. One or more ion species may be employed if desired. The fluency of ions implanted will usually be in the range of about $1\times10^{14}$ and $1\times10^{18}$ ions/cm$^2$. The ion accelerating energy will normally be in the range of about 10 and 1000 keV. Ion beam current will typically be below 1 μA/cm$^2$, more usually below 0.5 μA/cm$^2$ in order to avoid heating the implant excessively. Commercially available ion implantation equipment may be used.

The protein coating and ion implantation alter the surface properties of the metal implant. Surface properties that may be altered include, without limitation, thrombogenicity, and endothelial cellular migration and adhesion. As indicated previously, the protein coating and ion implantation at most only minimally (i.e., usually less than about 1%) increase the dimensions of the implants. In addition, the ion implantation improves the fixation of the protein coating on the metal surface.

The ion-implanted protein-coated implants of this invention may be placed within vessels using procedures well known in the art. Generally, the desired site within the vessel is accessed with a catheter. For small diameter tortuous vessels the catheter may be guided to the site through the use of guidewires (see, e.g. U.S. Pat. No. 4,884,579) or, in blood vessels, by flow-directed means such as balloons placed at the distal end of the catheter. Once the site has been reached the catheter lumen is cleared by removing the guidewire (if a guidewire has been used). In the case of occlusion coils, the coil is loaded into the proximal end of the catheter and advanced through the catheter by means of a pusher wire. The coil may be attached to the distal end of the pusher via a cleavable joint (e.g., a joint that is severable by heat, electrolysis, or other means) or a mechanical joint that permits the coil to be detached from the distal end of the pusher. Electrolytically severable joints are exemplified in U.S. Pat. Nos. 5,122,136; 5,134,295; 5,423,829; 5,522,836; and 5,624,449. A heat-cleavable joint is exemplified in U.S. Pat. No. 5,108,407. Mechanical joints are exemplified in U.S. Pat. Nos. 5,234,437; 5,250,071; 5,261,916; and 5,350,397. Alternatively, the coil may be detached from the pusher and simply pushed through the catheter and expelled from the distal end of the catheter.

In the case of stents, they may be loaded into the proximal end of the catheter and advanced through the catheter and released at the desired site in manners similar to those described above with respect to occlusion coils. Alternatively, they may be carried about the distal end of the catheter in a compressed state and released at the desired site. The stent may either be self-expanding or expanded by means such as an inflatable balloon segment of the catheter. After the implant(s) has been deposited at the desired intralumenal site, the catheter is withdrawn.

The following example further illustrates the invention. This example is not intended to limit the invention in any manner.

Coil Preparation:

Electrolytically detachable Pt coils (Guglielmi Detachable Coils; GDC, available from Target Therapeutics, Fremont, Calif. U.S.A.) of sizes 8×40, 8×20, 6×20, 5×15 (coil diameter (mm)×length (cm)) of "GDC-18" thickness (i.e., 0.015 in.); and size 4×10 of "GDC-10" thickness (i.e., 0.010 in.) were coated with either fibronectin (human plasma fibronectin, 0.5 mg/ml; Koken, Tokyo, Japan), type I collagen (bovine dermis collagen, 0.3%, Koken, Tokyo, Japan) vitronectin (bovine plasma vitronectin, 0.1 mg/ml; Koken, Tokyo, Japan), laminin (mouse laminin, 1.0 mg/ml; Koken, Tokyo, Japan) or albumin (human serum albumin, 50 mg/ml, Midorijuji, Osaka, Japan). The coating method entailed simply dipping the coils into the protein solutions and drying them for up to two hours. These coils underwent Ne+ ion implantation at a fluency of $1\times10^{15}$ ions/cm$^2$ at an acceleration energy of 150 keV. The beam current density was less than 0.5 μA/cm$^2$ to prevent excess heating of the coils. Standard non-coated Pt GDC coils were used as controls.

Aneurysm Construction:

Thirty four experimental aneurysms were constructed microsurgically in bilateral common carotid arteries of swine. The animal's neck was shaved and scrubbed with betadine solution, then draped in sterile fashion. Under sterile conditions, a 10 cm incision was made in the midline of the neck. Self-retractors were used to facilitate exposure. Reflecting the right sternocleidomastoid muscle medially, a 4 cm segment of the right external jugular vein was isolated at both ends with a ligature and then divided to form an open-ended vein segment, to be used as the venous graft. This vein was divided into two equal segments to make two aneurysms of equal size. Next, using a surgical microscope, a 3 cm segment of the right common carotid artery was exposed and cleaned of adventitia. Two small vascular clamps were then placed at each end of the isolated common carotid artery segment to achieve temporary vessel occlusion. A 7-mm-long arteriotomy was performed carefully and a venoarterial end-to-side anastomosis was made using 7–0 prolene. The aneurysms were almost all of equal size, ranging from 8 mm to 10 mm (mean: 9.0±0.7 mm). The second aneurysm was constructed in the left common carotid artery. During the procedure, the swine received $0.9–1.2\times10^6$ units of Penicillin G intramuscularly.

Aneurysm Embolization:

All endovascular treatments were undertaken in aneurysms immediately after their construction. Aneurysms maintained chronically (to assess their natural thrombosis or growth rate) before the embolization procedures were not used in this study. Instead, bilateral aneurysms were embolized in each animal, and the relative differences in wound healing between treatments using ion-implanted, protein-coated and standard GDCs were evaluated. Thus, it was felt that any underlying spontaneous growth/thrombosis would be similar in bilateral aneurysms and would have the same effect on both treatments.

A 6-F angiographic sheath was placed in the right femoral artery following standard Seldinger puncture and catheterization. Via this transfemoral route, a selective common carotid arteriogram was performed using a 6-F Fastguide catheter (Target Therapeutics), and the aneurysm outlined in multiple projections. A bolus 3000 U of heparin was injected to prevent thrombosis during the procedure. Next, a Tracker 18 microcatheter and Seeker 14 microguidewire combination (Target Therapeutics) were advanced coaxially through the guiding catheter and the tip of the microcatheter and positioned into the center of the aneuaneurysm sac. The aneurysms were embolized with standard GDCs on one side and with ion-implanted protein-coated GDCs on the contralateral side. Packing with coils was the goal of treatment for each aneurysm, to reduce the occurrence of persistent unobliterated portions of aneurysms and the effects of consequent hemodynamic inequalities that might affect the migration of endothelial cells across the aneurysm neck. To assume equal packing of different aneurysms with coils, the relative volume of metallic coil in relation to the volume of the aneurysms being embolized was calculated as: total length of the coils used in each aneurysm×(coil radius)$^2$×π/volume of aneurysm×100%. All aneurysms were assumed to be spherical for the purpose of this calculation. There was no statistical significant difference (p=0.3542, paired 2-tailed-test) between the ion-implanted, protein-coated GDC group (17.4±4.4%, n=10), and the standard GDC group (19.2±6.2%, n=10) at the day 14 post-treatment evaluation. One aneurysm was not treated and acted as a control (followed-up to 60 days after construction). The physical and performance characteristics of the ion-implanted, protein-coated GDCs were evaluated during the endovascular procedures.

Diagnostic angiography was performed at day 7, 14, 21, 30, and 60 after coil placement, after which each animal was euthanized using standard approved procedures. The parent arteries of specimens were cut length-wise, and the aneurysms orifice (as viewed from within the artery lumen) was observed macroscopically. The largest dimension of the orifice (OF) and the thick white fibrous membrane (FM) which covered the orifice were measured as the FM to OF ratio (and recorded as the FM/OF×100%). This evaluation was conducted on specimens 14 days after embolization (n=10 for standard group; n=10 for ionimplanted protein-coated group (n=2 with vitronectin, n=2 with collagen, n=2 with laminin, n=2 with fibrinogen, n=1 with albumin, n=1 with fibronectin)). In this study, particular attention was paid to the promotion of fibrous membrane coverage over the aneurysm orifice as a measure of wound healing acceleration. Statistical analysis of the FM to OF ratio was performed using a student t-test (paired 2-tail). Results were considered significant at p<0.05 and reported at the mean±SD. Any coverage of the aneurysm neck by a thinner clear membrane was also noted but not included in the statistical evaluation. The specimens were fixed with 2% formaldehyde and embedded in plastic resin. Sections 20 μm to 30 μm thick were then made using a diamond knife and the sections stained with hematoxylin and eosin.

Assessment of Acute Thrombogenicity

The average weights of thrombus accumulated on coils were 1.9±1.4 mg for standard coils, 8.0±5.5 mg for ion-implanted fibronectin-coated coils, 3.9±1.6 mg for ion-implanted collagen-coated coils, and 2.3±1.4 mg for ion-implanted albumin-coated coils. The weight of thrombus on the ion-implanted albumin- and collagen-coated coils did not differ significantly from that on standard coils (p=0.7720 for albumin; p=0.1420 for collagen). Thrombus accumulated on ion-implanted fibronectin-coated coils was significantly heavier than that on standard coils (p<0.0001).

Scanning Electron Microscopic Findings

An intense blood cellular response (mostly composed of platelets and red blood cells) was observed on all ion-implanted protein-coated coil surfaces. Fibronectin- and collagen-coated ion-implanted coils demonstrated a strong response. The ion-implanted non-thrombogenic albumin-coated GDCs also showed direct cell adhesion on their surfaces. The standard coils demonstrated a different blood cellular response; a layer of protein and fibrin-like substance was deposited between the coil gaps and blood cell adhesion (mainly leukocytes) was observed on the fibrin layer.

Physical and Performance Characteristics of Ion-implanted Coated GDCs

After ion implantation, the coil diameter was observed to be increased minimally, by approximately 1–10 μm. The basic physical characteristics of GDCs such as their softness, smoothness, and memory shape were affected minimally by the protein coating and ion implantation processes. No difference in average electric resistance was observed between normal GDCs (0.649 kΩ), and ion-implanted fibronectin-coated GDCs (0.645 kΩ). There was no untoward change in GDC performance (with regard to pushability, softness, and memory shape) during in vivo placement of the coils.

Macroscopic and Light Microscopic Findings of Treated Aneurysms

At day 7 post-embolization, neither standard GDCs not ion-implanted GDCs had an endothelial-like thin layer over their aneurysm orifices. No clear difference in performance between standard and ion-implanted GDCs could be detected at this stage of follow-up. On specimens examined 14 days post embolization, greater re-endothelialization and wound healing at the neck of the aneurysm were observed macroscopically. There was no statistical difference between the mean OF (7.2±0.8 mm) for the ion-implanted GDC group and the mean OF (6.8±0.6 mm) for the standard GDC group (p=0.19334, paired 2-tail). The mean FM to OF ratio was 69.1±10.7% for the ion-implanted GDC group and 45.6±18.0% for the standard GDC group (p=0.0035). Light microscopy showed that well organized fibrous tissue bridged the aneurysm's neck when using ionimplanted fibronectin-, vitronectin- and laminin-coated GDCs, whereas only a fibrin-like thin layer covered the standard GDC surface. At day 21, the necks of aneurysms treated with either standard or coated GDCs were almost covered with a thin membrane. Light microscopy showed that red blood cells were still observed on standard GDCs and ion-implanted albumin-coated GDCs. At day 30 follow-up, the orifices of standard GDC and ion-implanted GDC-treated aneurysms were covered completely with thick fibrous membrane and well organized fibrous tissue filled all aneurysms. Interestingly, the non-treated aneurysm showed enlargement of its sac at day 7. However, it showed shrinkage and partial thrombosis of the sac at day 21, and by day 60, the non-treated aneurysm was thrombosed completely.

Modifications of the above described modes for carrying out the invention that are obvious to persons of skill in the medical devices, protein chemistry, and ion implantation arts are intended to be within the scope of the following claims.

We claim:

1. An intralumenal implant comprising a body of a biocompatible material and an ion-implanted protein coating on the body.

2. The implant of claim 1 wherein the biocompatible material is selected from the group consisting of a metal, a bioabsorbable polymer, a bioabsorbable copolymer, a non-bioabsorbable polymer, and a nonbioabsorbable copolymer.

3. The implant of claim 2 wherein the implant is selected from the group consisting of an occlusion coil and a stent.

4. An occlusion coil comprising a coil of a biocompatible material and an ion-implanted protein coating on the coil.

5. The coil of claim 4 wherein the biocompatible material is selected from the group consisting of a metal, a bioabsorbable polymer, a bioabsorbable copolymer, a nonbioabsorbable polymer, and a nonbioabsorbable copolymer.

6. The coil of claim 4 wherein the protein is a cell adhesion protein.

7. The coil of claim 6 wherein the biocompatible material is a metal and the cell adhesion protein is selected from the group consisting of collagen, fibronectin, vitronectin, laminin, and fibrinogen.

8. The coil of claim 4 wherein the ion is selected from the group consisting of $He^+$, $C^+$, $N^+$, $Ne^+$, $Na^+$, $K^+$, $N_2^+$, $O_2^+$, $Kr^+$, $H^+$, and $Ar^+$.

9. The coil of claim 6 wherein the ion is selected from the group consisting of $He^+$, $C^+$, $N^+$, $Ne^+$, $Na^+$, $K^+$, $N_2^+$, $O_2^+$, $Kr^+$, $H^+$, and $Ar^+$.

10. The coil of claim 7 wherein the ion is $Ne^+$.

11. A method for occluding a site within a mammalian body lumen comprising placing one or more ion-implanted protein-coated occlusion coils at said site.

12. The method of claim 11 wherein the protein is a cell adhesion protein.

13. The method of claim 12 wherein the protein is selected from the group consisting of collagen, fibronectin, vitronectin, laminin, and fibrinogen.

14. The method of claim 11 wherein the ion is selected from the group consisting of $He^+$, $C^+$, $N^+$, $Ne^+$, $Na^+$, $K^+$, $N_2^+$, $O_2^+$, $Kr^+$, $H^+$, and $Ar^+$.

15. The method of claim 12 wherein the ion is selected from the group consisting of $He^+$, $C^+$, $N^+$, $Ne^+$, $Na^+$, $K^+$, $N_2^+$, $O_2^+$, $Kr^+$, $H^+$, and $Ar^+$.

16. The method of claim 13 wherein the ion is $Ne^+$.

17. The method of claim 11 wherein the mammal is a human and the body lumen is a wide-necked brain aneurysm.

18. A method for making an ion-implanted protein-coated intralumenal implant comprising:

a) providing an implant body of a biocompatible material;

b) coating the body with a protein to form a protein-coated implant body; and c) subjecting the protein-coated implant body to ion implantation.

19. The method of claim 18 wherein the fluency of ions used in step c) is in the range of about $1 \times 10^{14}$ and $1 \times 10^{18}$ ions/cm$^2$ and the accelerating energy used in step c) is in the range of about 10 and 1000 keV.

20. The method of claim 19 wherein the implant body is an occlusion coil or a stent and the protein is a cell adhesion protein.

* * * * *